United States Patent [19]

Pinnow et al.

[11] 4,170,997
[45] Oct. 16, 1979

[54] MEDICAL LASER INSTRUMENT FOR TRANSMITTING INFRARED LASER ENERGY TO A SELECTED PART OF THE BODY

[75] Inventors: Douglas A. Pinnow, Pacific Palisades; Anthony L. Gentile, Thousand Oaks, both of Calif.

[73] Assignee: Hughes Aircraft Company, Culver City, Calif.

[21] Appl. No.: 827,923

[22] Filed: Aug. 26, 1977

[51] Int. Cl.² .................... A61B 17/36; A61N 3/00
[52] U.S. Cl. .......................... 128/395; 123/4; 32/26; 32/40 R; 350/96.26
[58] Field of Search ............ 128/303.1, 395–397, 128/4, 5; 350/96.26; 32/26, 40 R, DIG. 7

[56] References Cited

U.S. PATENT DOCUMENTS

| | | | |
|---|---|---|---|
| 3,467,098 | 9/1969 | Ayres | 128/303.1 |
| 3,551,051 | 12/1970 | Salgo | 350/1.4 |
| 3,821,510 | 6/1974 | Muncheryan | 128/395 |
| 3,843,865 | 10/1974 | Nath | 128/395 |
| 4,072,147 | 2/1978 | Hett | 128/395 |

*Primary Examiner*—Robert W. Michell
*Assistant Examiner*—C. F. Rosenbaum
*Attorney, Agent, or Firm*—W. H. MacAllister; Allen A. Dicke, Jr.

[57] ABSTRACT

There is disclosed a laser instrument which uses an infrared fiber optical waveguide to transmit a high power carbon monoxide or carbon dioxide laser beam for treating a selected part of the body. In one important application of the instrument, the laser beam is transmitted to the interior of the human body to perform surgical functions.

7 Claims, 3 Drawing Figures

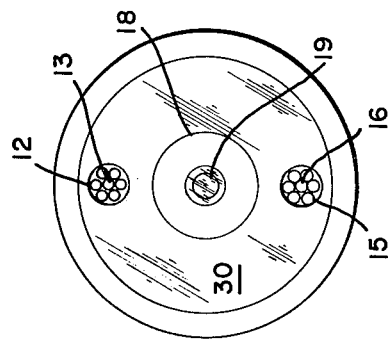
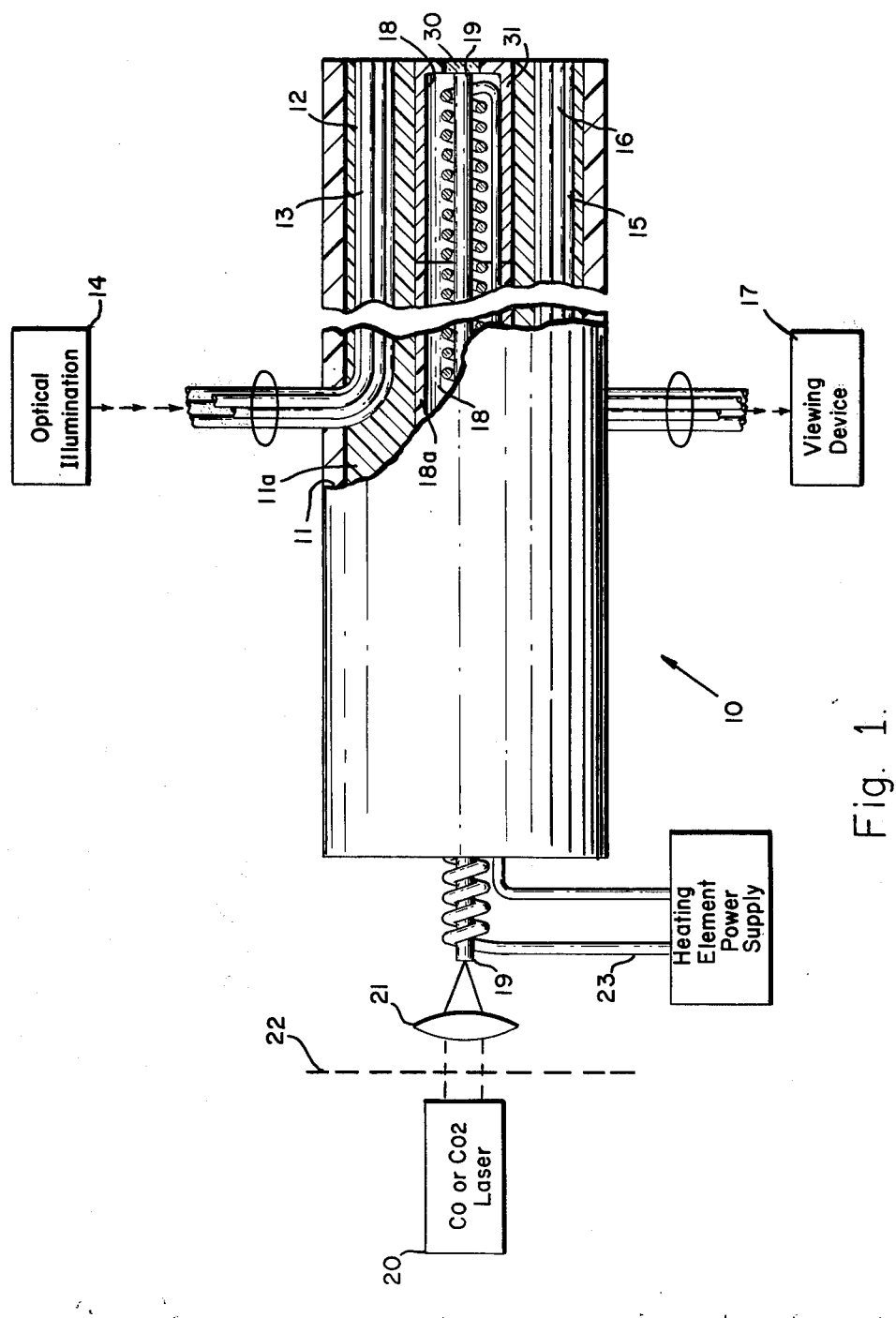
Fig. 2.
Fig. 1.

MEDICAL LASER INSTRUMENT FOR TRANSMITTING INFRARED LASER ENERGY TO A SELECTED PART OF THE BODY

BACKGROUND OF THE INVENTION AND PRIOR ART

There is a growing interest in the use of lasers for general dental, medical or surgical applications and it is generally believed that longer wave length laser beams, such as emitted from the carbon monoxide and carbon dioxide lasers at five and ten micrometers respectively, are preferred to the shorter wavelengths that are derived from the Nd: YAG and Argon ion lasers at 1.06 micrometers and 0.5 micrometers respectively. This preference with respect to surgical useage is due to the fact that the longer wave length radiation is highly absorbed by human tissues so that the illuminated zone is well defined and the extent of damage in cauterization is limited in depth to a single or few layers of cells. Although endoscopes for the purpose of observation of the interior of the human body have been well known for many years, there has heretofore been no practical way of delivering a CO or $CO_2$ laser beam to the inside of the body.

The development of a hollow metallic waveguide that can guide the $CO_2$ laser output has been reported by E. Garmire et al of the University of Southern California in Applied Physics Letters, Vol. 29 pp. 254–256, (1976). This guide, however, is considered excessively large in cross-section for most endoscopic treatment or surgical procedures.

There has recently been developed a new fiber optic waveguide suitable for transmitting infrared radiation which comprises a waveguide core formed from an extruded crystalline material which is a halide of a metal. This infrared transmitting fiber optical waveguide forms the subject matter of U.S. patent application, Ser. No. 800,149, filed May 24, 1977, on behalf of Douglas A. Pinnow et al entitled "Infrared Transmitting Fiber Optical Waveguide Extruded From Halides" and assigned to the assignee of the present application. The present invention pertains to means for safely and effectively using this new waveguide in a an instrument for applying laser energy to a selected part of the body.

SUMMARY OF THE INVENTION

It is an object of the present invention to provide a laser instrument capable in one of its applications of using long wavelength, high power laser radiation for surgical purposes inside the human body.

This object is achieved by providing a laser instrument of the type of an endoscope having at its core or center a fiber optic waveguide capable of infrared transmission in accordance with the teachings of the above-noted pending application. Means may also be provided to maintain the flexibility of the infrared waveguide and to couple laser radiation into it. The instrument is also provided with an optical illuminator and an optical viewing device to assist the operator in the performance of the surgery and with an end window to isolate the possibly toxic fibers from body fluids. Optionally, the device may also include a second low power laser in the visible region such as the helium-neon laser which can initially supply radiation through the central infrared fiber in order to precisely identify the point at which the infrared radiation will be applied for surgical purposes when an optical shutter is opened.

BRIEF DESCRIPTION OF THE DRAWINGS

These and other features, objects and advantages of the invention will be more fully apparent from the detailed description below taken in conjunction with the accompanying drawings wherein like reference characters refer to like parts throughout and in which:

FIG. 1 is a broken sectional and diagramatic view of a laser instrument of the form of an endoscope and embodying the principles of the present invention.

FIG. 2 is an end view of the instrument of FIG. 1.

DETAILED DESCRIPTION OF THE INVENTION

Figure 3:
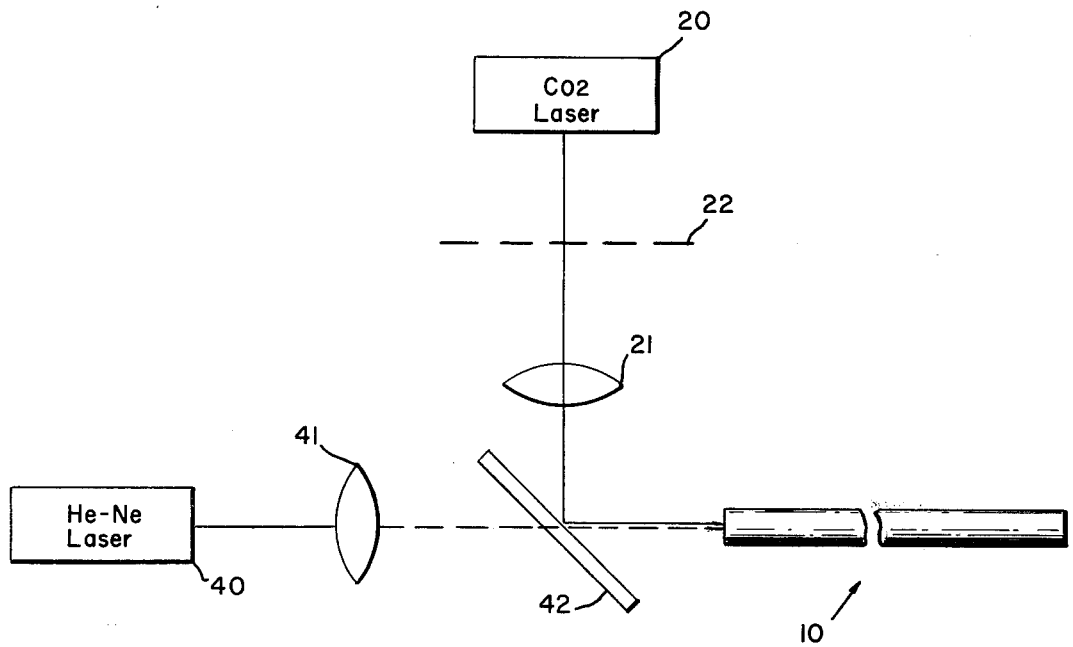
FIG. 3 is a view similar to FIG. 1 showing manner of using the spotting laser through the central infrared fiber.

The instrument shown in diagramatic cross-section in FIG. 1 combines the features of existing flexible fiber optical endoscopes designed for viewing with the ability to relay a high power infrared CO or $CO_2$ laser beam for surgical functions, such as cauterizing, cutting, or the like. For example, the instrument 10 may comprise a flexible outer sheath 11 surrounding a flexible body 11a in which there is formed a first hollow tube 12 containing a conventional glass fiber optical waveguide bundle 13 through which illumination from a source 14 is transmitted from the control end of the instrument to the output end thereof to provide illumination of the internal organ or other part of a body to be inspected and treated. A second tube 15 contains a second conventional bundle of glass optical fiber waveguide 16 which connects to a viewing device 17 by means of which the user is able to view the area illuminated by light from the source 14. A third hollow tube 18 is formed axially of the center of the body of instrument 10. It is lined by plastic member 18a and contains a flexible infrared transmitting fiber optical waveguide 19 which is optically coupled to a carbon monoxide or carbon dioxide laser 20 by a lens or other suitable means 21. An optical shutter 22 of any convenient design is interposed between the lens and the laser so that the output of the laser can be turned on and off in accordance with the needs of the surgical function desired. If the material from which the fiber optic infrared transmitting waveguide 19 is formed is not itself flexible at room temperature, a heating element 23 may be spirally wound around the fiber 19 and connected to a heating element power supply 24 so as to raise its temperature to normal body temperature or above to render it flexible in a manner which will be discussed below.

Since the material from which fiber 19 is made may be toxic, it should not be permitted to have direct contact with body fluid or tissue. Hence, an inert window 30 is provided at the termination end of the fiber. Window 30 is sealed to a holding collar 31 which firmly joins the plastic jacket 18a which surrounds the tube 18. The seal can be a solder joint to a metal collar or some equivalent leak tight seal. The window 30 should have low absorption for infrared wavelengths in order to usefully transmit high power surgical CO and $CO_2$ laser beams as well as the visible wavelength beams. Of the many possible window materials it has been found that only diamond (presently limited to natural diamond for optical transmission) and zinc selenide are suitable for the present application. The high strength of diamond makes it a preferred material for use with a $CO_2$ laser source.

Both diamond and zinc selenide have essentially no solubility in fluids with which they may come into contact in the body. Diamond transmits throughout the visible spectrum and ZnSe transmits from 5000 Å; at 10.6 μm. The absorption coefficient of diamond is $\beta < 0.05$ cm$^{-1}$ and ZnSe at 10.6 μm $\beta = 4 \times 10^{-4}$ cm$^{-1}$. At 5.3 μm the absorption coefficient of ZnSe remains the same however, diamond has an absorption in this region. Both are high index of refraction materials, e.g. at 10.6 μm, ZnSe $n = 2.40$, diamond $n = 2.39$. Because of the high refraction index of diamond and ZnSe, it is advantageous to have the infrared window 30 anti-reflection coated to maximize light transmission. The interior coating can be any standard coating. However, the exterior coating must be inert to body fluids, such as $BaF_2$/ZnSe multilayers.

The optical fiber 19 used to transmit the infrared radiation from laser 20 is preferably of the type disclosed and claimed in U.S. patent application, Ser. No. 800,149, filed May 24, 1977, by Douglas A. Pinnow et al entitled "Infrared Transmitting Fiber Optical Waveguide Extruded From Halides" and assigned to the assignee of the present application. The fibers therein disclosed comprise a waveguide core formed from an extruded crystalline material which comprises a halide of a metal selected from Groups IA, IB, or IIIA of the periodic table and which core is surrounded by means for optically confining guided radiation modes therein which may, for example, comprise a loose fitting polymer cladding. Such waveguides wherein the core is fabricated by extrusion using heavy bionic compounds and selected from the above noted metal halides are particularly suited for infrared radiation transmission at extended wavelengths. The range of transparency may extend to approximately 35 micrometers. Typically preferred heavy ionic compounds are thallium bromide (Tl Br) and thallium bromoiodide ($Tl,Br_x,I_{1-x}$). Although conventional fiber drawing techniques cannot be used to prepare these materials into optical fibers, it has been found that it is possible to extrude these materials into fibers through a small orifice die at elevated temperatures and high pressures and that these fibers may be fabricated to and will perform as radiation waveguides at extended infrared wavelengths in the range of 0.6 micrometers to 35 micrometers. The diameter of the orifice in the extrusion die is such that the polycrystalline fibers have been prepared with core diameters in the range of 100-500 micrometers. The extrusion temperature for thallium bromoiodide (KRS-5) ranged from 200° to 350° centigrade (which is below the 414° centigrade melting point of KRS-5) and the extrusion rates were approximately several centimeters per minute. Losses in the waveguide are limited both by impurity absorption an by scattering from waveguide imperfections. Total absorption losses of less than $10^{-2}$ inverse centimeters have been observed at 10.6 micrometers and a two-watt continuous $CO^2$ laser beam has been transmitted through a test fiber without degradation. The KRS-5 fibers possess remarkable "plastic" like properties in the temperature range of 250° to 350° centigrade. In this range the fibers can be bent into almost any arbitrary configuration which can be permanently set when the fiber is cooled to room temperature. The mechanical characteristics of the thallium bromide fibers are much different. Their temperature range of plasticity extends below room temperature and these fibers are extremely flexible at the ambient temperatures. They do not require the use of the heating element 23 and are thus preferred.

However, if the KRS-5 bromoiodide fiber is used, it is necessary to use the heating element 23 to maintain its temperature in the range of plasticity. When such an arrangement is used, it will, of course, be understood that the material 11 in which the hollow tubes are formed should be selected to be an excellent heat insulator and temperatures must be carefully controlled to prevent unintended patient injury.

An additional feature which can be advantageously added to the instrument shown in FIG. 1 is a low power helium-neon laser 40 shown in FIG. 3. This low power laser 40 can be optically coupled to the infrared fiber 19 by means of a glass lens 41 which transmits its output through a dielectric glass plate 42 to the fiber 19 in order to provide a visual indicator to the surgeon of the region that will be illuminated when the infrared laser is energized. The glass plate 42 is dielectrically coated for high reflectivity of $CO_2$ emission at 10.6 micrometers and for high transmission of He-Ne emission at 0.63 micrometers. The $CO_2$ laser 20 is arranged to transmit its output through germanium lens 21 to be reflected from plate 42 into the fiber 19 when the shutter 22 is opened. The plate 42 is shown at a 45° angle to the axis of waveguide 19 which is also the axis of the helium-neon laser 40. The axis of the $CO_2$ laser 20 is at right angles and intersects with the axis of the waveguide 19 and the plate 42.

During normal operation, the surgeon will leave the helium-neon laser on continuously to aid in the positioning of the endoscope. After the desired alignment has been accomplished the surgeon will "fire" the high power infrared $CO_2$ laser 20 in a short burst by opening the shutter 22. FIG. 3 shows only one way for simultaneously coupling the helium-neon laser and the $CO_2$ laser into the infrared transmitting fiber 19. Of course, it will be understood that other equivalent arrangements may be used.

A test has been conducted in which a $CO_2$ laser was optically coupled to a thallium bromoiodide core fiber optical waveguide using a germanium lens 21. An optical shutter 22 was used to turn the laser beam on and off. When the shutter was opened, approximately one watt of ten micrometer radiation was coupled into the fiber, transmitted along its length and reradiated from its output end. A piece of paper was placed near the output end of the fiber to simulate human tissue. When the shutter was opened, a small hole was burned through the paper. The fiber end could be moved around to burn selected areas of the paper. It is thus seen that the instrument is suitable in one mode of operation for use as a surgical endoscope.

What is claimed is:

1. In a medical laser instrument having an output end for transmitting laser energy to a selected part of the body, the improvement comprising:
    (a) fiber optic waveguide means comprising a polycrystalline halide of a metal, enclosed in said instrument for transmitting an infrared laser beam for performing operations on a selected part of the body with infrared radiation and for transmitting a visible laser beam,
    (b) an infrared laser coupled to said fiber optic waveguide means,
    (c) a low power laser having an output wave-length in the visible region of the spectrum and coupled to said fiber optic waveguide to provide a visible indication on said selected part of the body of a point at which infrared radiation from said waveguide will be applied, and (d) a diamond window inert to body fluids, sealed to the output end of said instrument for transmitting radiation from both said infrared laser and said low power laser and for isolating said polycrystalline halide from the body.

2. In a medical laser instrument for transmitting laser energy to a selected part of the body, the improvement comprising:

(a) infrared transmitting fiber optic waveguide means enclosed in said instrument for transmitting an infrared laser beam for performing operations on said selected part of the body, and (b) heating means disposed adjacent to said infrared transmitting fiber optic waveguide to supply heat thereto to increase the flexibility of said waveguide.

3. In a medical laser instrument for applying laser energy to a selected part of the body, the improvement comprising:

(a) infrared transmitting fiber optic wave-guide means enclosed in said instrument for transmitting an infrared laser beam for performing operations on said selected part of the body with infrared radiation, (b) an infrared laser, (c) means disposed in the path between said infrared laser and said waveguide for coupling the output of said infrared laser to said waveguide, and (d) shutter means disposed in said path to selectively control the transmission of the output of said infrared laser to said waveguide.

4. In a medical laser instrument for transmitting laser energy to a selected part of the body, the improvement comprising:

(a) infrared transmitting fiber optic waveguide means enclosed in said instrument for transmitting an infrared laser beam for performing operations on said selected part of the body with infrared radiation and for transmitting a visible laser beam, (b) an infrared laser coupled to said infrared transmitting fiber optic waveguide, and (c) a low power laser having an output wavelength in the visible region of the spectrum and coupled to said infrared transmitting fiber optic waveguide to provide a visible indication of a point on a surface of said part of the body at which infrared radiation from said waveguide will be applied.

5. A medical instrument as in claim 4 wherein both said low power laser and said infrared laser are coupled to said infrared transmitting fiber optic waveguide by means of a dielectric beam splitter which transmits radiation having a wave length of the output of said low power laser and which reflects radiation having a wave length of the output of said infrared laser, said infrared laser being positioned to have its output reflected from said dielectric beam splitter into said infrared transmitting fiber optic waveguide and said low power laser being positioned to have its output transmitted through said dielectric beam splitter into said infrared transmitting fiber optic waveguide.

6. A medical instrument as in claim 5 wherein said low power laser is a helium-neon laser and said infrared laser is a carbon monoxide laser.

7. A medical instrument as in claim 5 wherein said low power laser is a helium-neon laser and said infrared laser is a carbon dioxide laser.

* * * * *